(12) United States Patent
Kahle

(10) Patent No.: US 11,234,906 B2
(45) Date of Patent: Feb. 1, 2022

(54) COSMETIC PREPARATION IN GEL FORM

(71) Applicant: SCHWAN-STABILO COSMETICS GMBH & Co. KG, Heroldsberg (DE)

(72) Inventor: Ingolf Kahle, Rückersdorf (DE)

( * ) Notice: Subject to any disclaimer, the term of this patent is extended or adjusted under 35 U.S.C. 154(b) by 125 days.

(21) Appl. No.: 16/470,159

(22) PCT Filed: Dec. 15, 2017

(86) PCT No.: PCT/EP2017/083073
§ 371 (c)(1),
(2) Date: Jun. 14, 2019

(87) PCT Pub. No.: WO2018/109175
PCT Pub. Date: Jun. 21, 2018

(65) Prior Publication Data
US 2019/0358132 A1    Nov. 28, 2019

(30) Foreign Application Priority Data
Dec. 15, 2016   (DE) .......................... 2020161070015

(51) Int. Cl.
| A61Q 1/10 | (2006.01) |
| A61K 8/04 | (2006.01) |
| A61K 8/19 | (2006.01) |
| A61K 8/37 | (2006.01) |
| A61K 8/81 | (2006.01) |
| A61K 8/87 | (2006.01) |
| A61K 8/89 | (2006.01) |

(52) U.S. Cl.
CPC ............... *A61K 8/042* (2013.01); *A61K 8/19* (2013.01); *A61K 8/375* (2013.01); *A61K 8/8117* (2013.01); *A61K 8/8152* (2013.01); *A61K 8/87* (2013.01); *A61K 8/89* (2013.01); *A61Q 1/10* (2013.01); *A61K 2800/43* (2013.01); *A61K 2800/524* (2013.01); *A61K 2800/872* (2013.01)

(58) Field of Classification Search
None
See application file for complete search history.

(56) References Cited

U.S. PATENT DOCUMENTS

| 2007/0104677 | A1  | 5/2007  | Dold |
| 2010/0111884 | A1  | 5/2010  | Acker et al. |
| 2011/0171151 | A1* | 7/2011  | Arnaud .................... A61K 8/91 424/63 |
| 2012/0258059 | A1* | 10/2012 | Iwama ................. A61K 9/0014 424/59 |
| 2013/0171083 | A1  | 7/2013  | Li et al. |
| 2015/0265504 | A1  | 9/2015  | Crane et al. |
| 2015/0342845 | A1* | 12/2015 | Hwang .................. A61K 8/375 424/60 |
| 2016/0136060 | A1  | 5/2016  | Crane et al. |
| 2016/0235661 | A1* | 8/2016  | Changoer .............. A61K 8/347 |

FOREIGN PATENT DOCUMENTS

| DE | 102004027838 A1 | 12/2005 |
| WO | 2016046399 A1 | 9/2016 |

OTHER PUBLICATIONS

International Search Report and Written Opinion of International Searching Authority of PCT/EP2017/083073.

\* cited by examiner

*Primary Examiner* — Jyothsna A Venkat
(74) *Attorney, Agent, or Firm* — Bradley Arant Boult Cummings; Timothy L. Capria; Alexandra C. Lynn

(57) ABSTRACT

The invention relates to a cosmetic composition for application in the eye area in the form of a gelatinous emulsion, and to the preparation and use thereof.

10 Claims, 3 Drawing Sheets

COSMETIC PREPARATION IN GEL FORM

Figure 1:
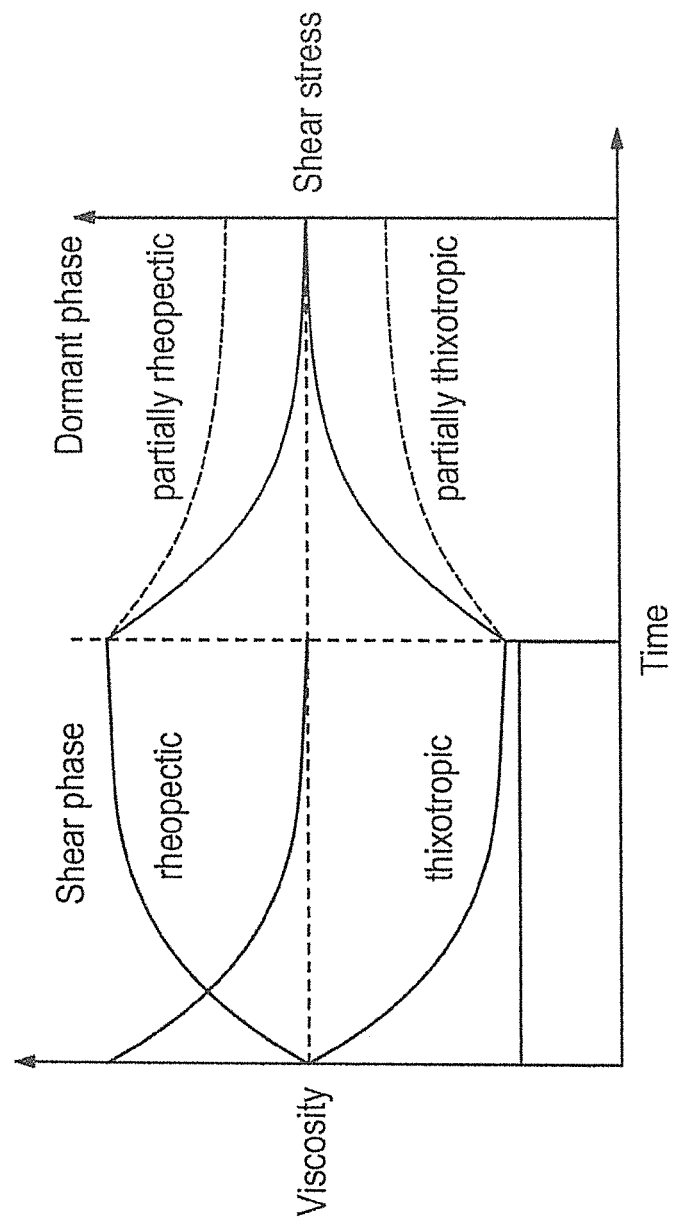

The present invention relates to a cosmetic composition to be applied to the eye area in the form of a gelatinous emulsion and to the production and use thereof.

Cosmetic preparations for making up the skin or the semi-mucous membranes are commonly known in the form of makeup pencils, as soft pastes, or in the form of loose or pressed powders. Makeup pencils or pastes often come in an anhydrous form as mixtures of vegetable, animal, or synthetic oils, fats, and waxes in which a powder phase of pigments, pearlescing agents, and fillers approved for cosmetics is dispersed. Pressed powders often consist of mixtures of pigments, pearlescing agents, and fillers with an oil- or emulsion-based binder that is added to make them easier to handle and process. There are cosmetic preparations in the form of an emulsion for various applications and in many variations from liquid to solid.

General requirements of compositions in the field of decorative cosmetics are a long shelf life of the composition, simple application, a pleasant feel when applied to the skin or semi-mucous membrane, long adherence to the applied location, and no smearing or migration in wrinkles.

Many known preparations have the disadvantage that they do not adhere well to the applied location and can be easily transferred to materials such as dishes, cutlery, glass, textiles, or skin. As a result, these preparations must be reapplied repeatedly. Since oils spread on the skin and on semi-mucous membranes and also have a different spreading capacity, ingredients of these preparations, especially pigments, can migrate into the fine folds of the skin around the lips or eyes and create unwelcome structures. Skin sebum and perspiration can cause or intensify these effects. In the case of preparations applied in the region of the eye, a "touch-up" is also a problem, because the movement of the eyelids and the effect of the sebum cause part of the applied mass, such as eyeliner or eyeshadow, to migrate into the folds of the eyelid in particular, producing strip-like structures.

Attempts have also been made to eliminate oils, fats and waxes and to produce aqueous or aqueous-alcoholic preparations in the form of dispersions containing polymers that form elastic and more or less water-resistant films on the skin or semi-mucous membranes. However, such preparations cause other problems, as the films dry slowly and are not always comfortable on the skin.

Emulsions are known to be used for cosmetic preparations. However, emulsions often do not provide satisfactory durability on contact with water or endogenous fluids, such as sweat or sebum.

The ability to provide cosmetic preparations that are applied to the eye is particularly demanding. On the one hand, durability requirements are particularly high here, but are difficult to satisfy because of increased moisture around the eye. On the other hand, the eye area is particularly sensitive. Therefore, the provision of kohl and eyeliner preparations that are applied to the eye or to the waterline of the eye is particularly demanding; such products require contradictory properties. Because of their hardness and low abrasion, wax-based kohl pencils are often uncomfortable and difficult to apply or, if abrasion is better after application, have insufficient durability and smudge resistance.

Alternatively, there are liquid compositions that contain film formers. Here, however, the application to the waterline creates a strong burning sensation and an unpleasant feeling if the kohl mass gets into the eye. Furthermore, the line applied to the eye may smear if the water resistance is insufficient and/or parts of the mass may migrate away from the application site. For example, a liquid kohl preparation is known to be applied with an applicator by drawing a plastic pencil with the kohl mass between the closed eyelids in such a way as to distribute the kohl mass over the lower and upper waterlines. Both the durability and the precision of the application are a problem with this product.

To overcome some of the known problems, U.S. Pat. No. 2,013,017 1083 describes a cosmetic composition to be applied to keratinous tissue that contains a polyvinyl alcohol/styryl pyridinium polymer and a latex film former. UV radiation or visible light are to be used to cure the composition and thus to obtain durability. However, this is difficult to apply to the eye area. The compositions described are intended especially as nail polish for which simple, precise, and pleasant applicability to the waterline is not a problem.

In order to obtain a durable composition, US 2010 011 1884 discloses a cosmetic preparation in which film-forming copolymers produce either a water-resistant or an oil-resistant film. A variety of ingredients is offered to solve different problems. Compositions that are mentioned specifically are sunscreen products.

The object of the invention is therefore to provide a liquid preparation that is smudge-, water-, and oil-resistant, as well as easy and comfortable to apply.

Furthermore, it was an object of the present invention to provide a preparation that is easy and comfortable to use in sensitive areas such as around the eye and that remains water-, oil-, and smudge-resistant, and durable after application, that does not burn or irritate the eyes, that dries quickly, and that produces strong, lasting coloring. In addition, the applied mass should also be easy to remove again.

These objects are achieved with a preparation as defined in the claims.

The invention relates to an emulsion-based cosmetic preparation in the form of a gel that comprises:
  a) a lipid phase comprising at least one poly(acrylate-co-siloxane)-based film former and at least one solvent
  b) an aqueous phase comprising at least one water-soluble or water-dispersible film former based on acrylate or polyurethane and an aqueous medium
  c) at least one emulsifier based on polyglyceryl fatty acid ester
  d) at least one pigment.

It has been found that the preparation according to the present invention has an advantageous combination of properties that makes it particularly suitable for use on the eye. One advantage is that the composition is thixotropic, i.e. it is thin when shear is applied and gelatinous in a dormant state. This allows a particularly simple application in the eye area because, for one thing, not too much mass is removed, but the extracted mass can be very easy to apply because of its consistency. In addition, it has surprisingly been found that the applied mass neither runs nor rubs off after drying. It is smudge-proof and resistant to migration. The emulsion-based preparation according to the present invention has low viscosity even at low shear forces, so that it can be applied easily and comfortably, for example, at the waterline of the eye. After the application, the thixotropic mass solidifies again up to the initial viscosity and remains stable on the place of application. Furthermore, the composition according to the present invention can be adjusted rheologically by the rate and type of film former so that it is in liquid form or in solid form at room temperature. The special combination of ingredients allows quick drying and the film produced is not only water-, oil-, and smudge-resistant and extremely durable, but also forms a kind of matrix in which the other ingredients, in particular the pigments, are homogeneously embedded so that they remain on the applied spot and form a well covering, even film. The film formed after application prevents migration of ingredients of the preparation and provides intense uniform coloring because the pigments are homogeneously distributed throughout the gelatinous preparation. Make-up removal presents no problems, despite the good durability. The film formed after application of the preparation according to the present invention can be removed by known means such as make-up removal pads or wipes.

Because of these advantageous properties, the emulsion preparation according to the present invention is particularly suitable for use on the eye and can be used especially as kohl or eyeliner.

Figure 2:
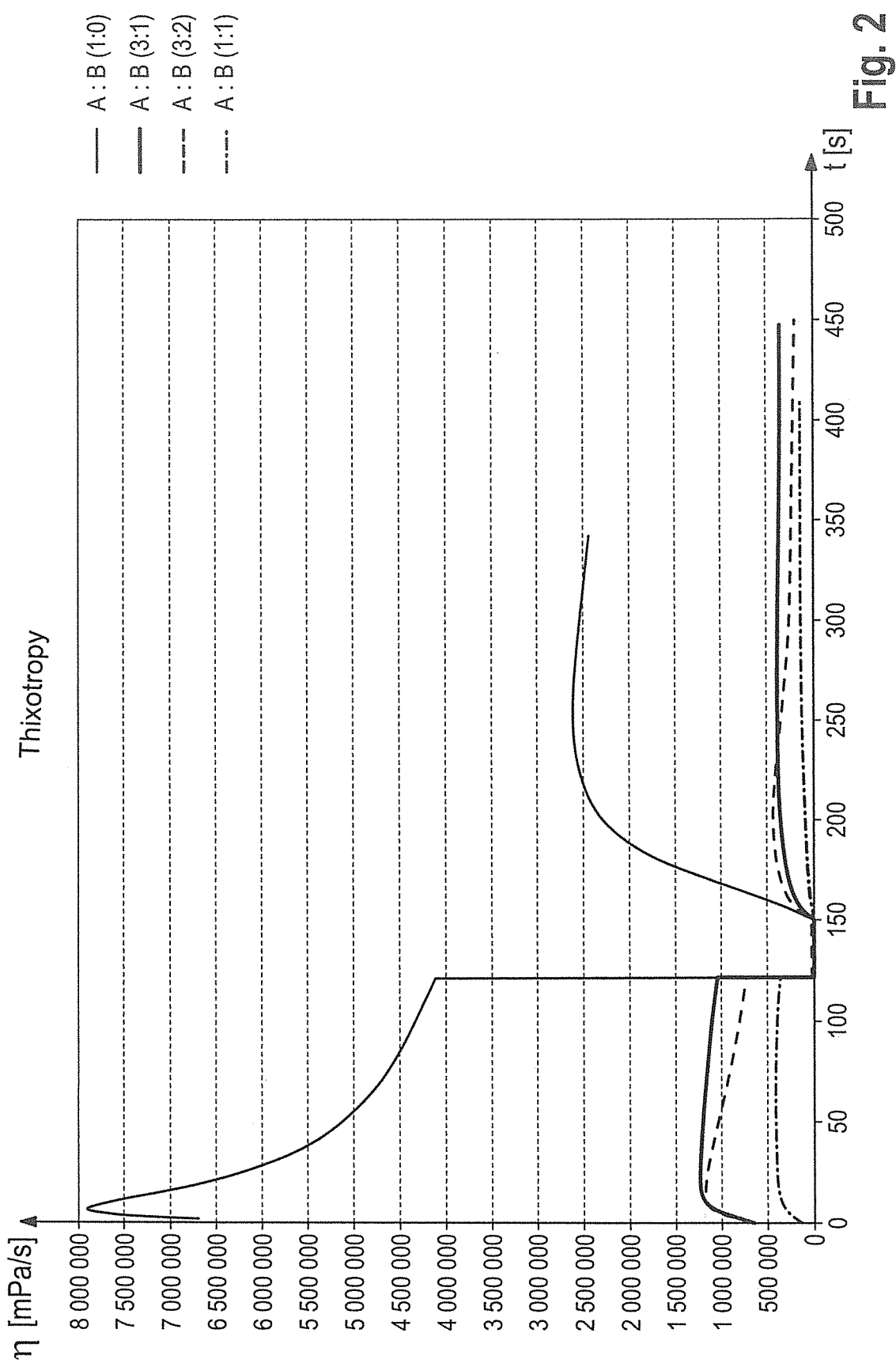
Figure 3:
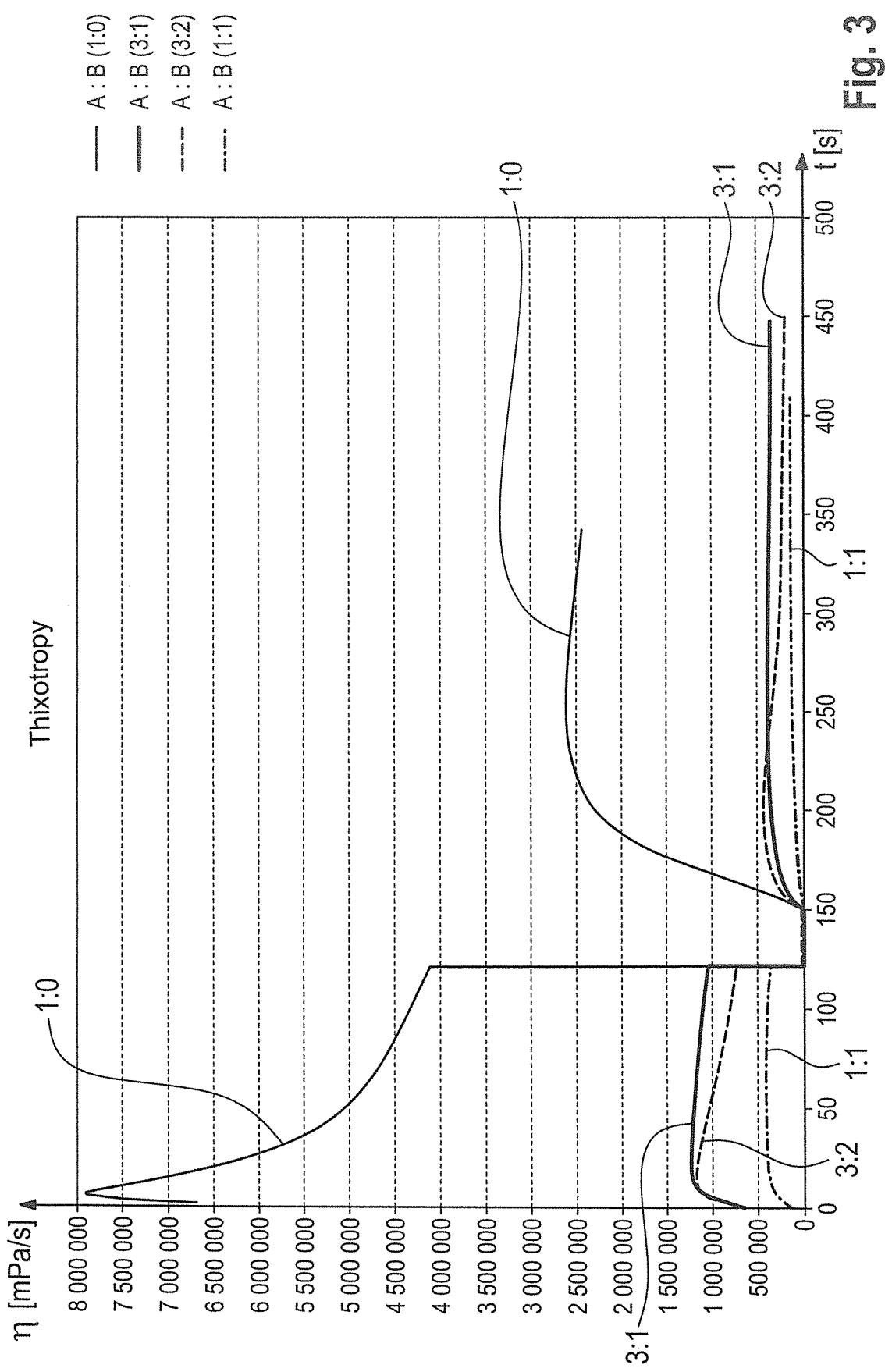

The drawings serve to illustrate the invention, wherein:

FIG. 1 shows the viscosity profile of thixotropic and rheopexic fluids and;

FIG. 2 and FIG. 3 show a rheogram for different masses with varying ratios of two film former dispersions A to B (FIG. 3 with arrows for better identification). The curve shows the viscosity based on the time, wherein a shear rate of $0.1\ s^{-1}$ was used for 120 s, then increased to $100^{-1}$ for 30 s and then reduced again to $0.1^{-1}$. The rapid drop in viscosity to almost zero at a shear rate of $100\ s^{-1}$, as well as the rapid increase in viscosity upon completion of the shear strength, demonstrate the pronounced thixotropy of the system. Also the influence of the components on the viscosity is very easy to recognize.

DEFINITIONS

Here, "application location" refers to the surface to which the preparation according to the present invention is applied. The application location is in particular the area of the eyes, such as the eyelids, the edge of the eye, or the waterline of the eye.

As used herein, the term "gel" generally describes a disperse system consisting of at least two components, wherein a solid component forms a spongy, three-dimensional, continuous pore system or network, these pores being filled by one or more fluids, and wherein these pores can also contain other ingredients, such as pigments, for example.

The preparation according to the present invention is in the form of a thixotropic gel, i.e. a gel in which interactions are minimized by relatively low external shear, causing a sudden decrease in viscosity and thus liquefaction. After completion of the shear, the material can return to the viscous initial state. The thixotropic gel may be liquid or solid in its dormant state.

The term "emulsion" as used herein describes a dispersed system of an aqueous and a lipid phase that additionally contains an emulsifier. The aqueous phase is also referred to as the water phase and contains at least water as a carrier and at least one hydrophilic film former. The lipid phase contains at least one solvent as a carrier and at least one hydrophobic film former. Emulsions of the present invention may be oil-in-water or water-in-oil emulsions, depending on the mass fraction percentages. The term "emulsion" also refers to microemulsions in which the disperse phase is present in droplet form with diameters in the micro- to nanometer range. Double emulsions such as oil-water-oil or water-oil-water emulsions are also included.

The terms "dispersed" and "dissolved" are used equivalently in conjunction with polymers. Because the transitions between dispersion and solution for polymers often cannot be determined, polymer dispersion is understood to mean a composition in which the polymer is compatible with the solvent, does not settle, and therefore is dissolved and/or dispersed, and does not separate.

A "hydrophilic film former" is a polymer that is compatible with water, i.e. it can be dispersed or dissolved in an aqueous medium, such as water or an aqueous solvent, and forms a film after application.

A "hydrophobic film former" is a polymer that is compatible with an organic solvent and can be dispersed or dissolved in a solvent and form a film after coating.

Film formers, both hydrophilic and hydrophobic, are generally used in the form of a dispersion/solution. The amounts given for film formers in the description refer in each case to the polymer itself, not to the amount of dispersion.

Unless otherwise indicated, the percentages are based on the total amount of the preparation in each case.

The term "solvent" when used here refers to organic solvents, such as those used for the solution/dispersion of the hydrophobic film former and does not include water. When the amount of solvent in the preparation is indicated, it refers to the total amount of solvent added directly and to the solvent added as part of a dispersion. A "solvent" can be a solvent or a mixture of solvents.

A "volatile solvent" is one having an evaporation number of 100 or less. The volatility or evaporation number refers to the ratio of the vapor pressure of the solvent in question to the vapor pressure of diethyl ether, each measured at 20° C. and 65±5% relative humidity. The evaporation number can be determined according to DIN 53170.

The viscosity was measured at room temperature. The term "room temperature" usually refers to a temperature of 25° C.

The emulsion preparation according to the present invention contains, as components essential to the invention, a lipid phase, an aqueous phase, and a specific emulsifier as well as at least one pigment, and may additionally contain further ingredients common to cosmetics, such as plasticizers and preservatives. The components according to the present invention produce an emulsion that exhibits thixotropic behavior. Without wishing to be bound by theory, it is assumed that the interaction of the film formers used according to the present invention with the specific emulsifier forms a network in which solvents and oil-soluble components are embedded, thereby forming a gel. Volatile solvent and water evaporate at the temperature prevailing in the application area, i.e. at about 30° C. to 35° C. After evaporation, a polymer film remains, which is very durable and in which the other ingredients are embedded so that they cannot dissolve or be smeared. This produces a matrix in which the pigments are embedded homogeneously. This results in a uniform, full coloration with good opacity.

The viscosity and thixotropy of the composition depend on the ingredients used and their proportions. It has been found that increasing the proportion of hydrophobic film former increases the thixotropy. However, without the presence of a hydrophilic film former, thixotropy does not occur or does not occur to an adequate extent. Hydrophobic ingredients, such as plasticizers, emollients, and oils that are commonly used in cosmetic compositions, may enhance the interaction, but may have a negative impact on the shelf life if they are present in too high a proportion.

The interactions between the ingredients essential to the invention are structured in such a way that the emulsion preparation according to the present invention liquefies as soon as low shear forces are used, for example, when applied, producing a thin liquid mass that can be easily applied and becomes gelatinous again on the applied location. This is the only reason why it can be applied as kohl to the waterline of the eye or as eyeliner to the moist skin around the eye without running and smudging and adheres for a long time.

The type and amount of the ingredients of the emulsion preparation according to the present invention, especially the type and amount of the film formers, can be selected to adjust the consistency of the emulsion to be liquid or solid. As a solid, it can be formed into a pencil lead, which can then be inserted in an applicator as a kohl or eyeliner pencil.

The film formers are important components of the preparation according to the present invention. Here, "film former" is generally understood to be a polymer, copolymer, or a mixture thereof, that forms a film on the applied location after the application and evaporation of the water or solvent. According to the present invention, two film-forming components are used—a hydrophilic and a hydrophobic component that interact, producing the thixotropy of the system and thus a smudge-resistant film on the applied location. The hydrophobic film former is part of the lipid phase while the hydrophilic film former is part of the aqueous phase.

The emulsifier is an ingredient essential to the invention. The choice of a suitable emulsifier is important in order to sufficiently homogenize the lipid phase and the aqueous phase of the present invention so that they remain homogeneously mixed over a broad temperature range in which the preparation must be stable. In addition, the emulsifier also contributes to the thixotropy of the preparation. Therefore, the choice of emulsifier is critical. The products must be stable at the temperature of the environment. Therefore, the temperature range essential for such products extends from −20° C. and below to 40° C. and above. It is also important that both the preparation and the film formed therefrom be stable at the temperature of the application location, i.e. on the eye, and thus at about 31° C. to 35° C.

It has been found that compounds based on polyglyceryl fatty acid esters have an excellent emulsifying effect when used together with a lipid phase and an aqueous phase. An example of an emulsifier according to the present invention is a natural product commercially available as Emulium Mellifera, which is a mixture of polyglyceryl-6 distearate, jojoba esters, polyglyceryl-3 beeswax, and cetyl alcohol, and other ingredients. Further examples of suitable emulsifiers according to the present invention are polyglyceryl di-fatty acid esters, especially diesters, of saturated or mono- or polyunsaturated C16-C20 fatty acids, such as polyglyceryl distearates and polyglyceryl dioleates. The following esters have proven to be very suitable (identified by INCI names): polyglyceryl-5 dioleates, polyglyceryl-10 diisostearates, polyglyceryl-6 distearates, and polyglyceryl-3 beeswax.

The mass fraction percentage of the emulsifier in the total composition of the preparation according to the present invention is 1 to 10% by mass, preferably 1.5 to 7.5% by mass, particularly preferably 2 to 5% by mass. The exact mass fraction percentage of the emulsifier depends on the chemical nature of the other components and the emulsifier used in each case. A specialist can determine the most suitable amount in each case in simple routine tests.

If too small an amount of emulsifier is used, no homogeneous emulsification takes place.

Another essential component of the preparation according to the present invention is the lipid phase, which comprises at least one organic solvent and at least one film former dispersed or dissolved therein. This film former is also referred to as a "hydrophobic film former". The hydrophobic film former is a polymer with acrylate and siloxane moieties. It has been found that a copolymer with siloxane moieties provides a sufficiently hydrophobic film while the acrylate moieties can interact with the acrylate groups of the water-compatible film former.

The amount of hydrophobic film former has an influence on the thixotropic properties and the consistency of the preparation, and is adjusted accordingly depending on the desired product. If the amount is below about 3%, a sufficiently stable film will not be the result, i.e. the resulting film will not be friction resistant. If the proportion of hydrophobic film former is too high, it will be difficult or even impossible to achieve a homogeneous mass or a homogeneous film. A suitable amount of the hydrophobic film former is in a range from approximately 3% to about 30% by mass, preferably 5% to 20% by mass, particularly preferably 8% to 18% by mass, based in each case on the proportion of polymer in the total mass.

The film former is usually used in the form of a solvent dispersion. Such dispersions are well known and commercially available. Typical film former dispersions have a polymer content of 30% to 60% by mass, for example, 40% by mass. So that the proportion of solvent in the finished preparation does not become too high, it is preferable to use film former dispersions that have a polymer content in a range from 40% to 60% by mass. Accordingly, a suitable amount of film former dispersion (i.e. polymer and solvent) used for a composition according to the present invention is in a range from 5% to 50% by mass, preferably 10% to 35% by mass.

In addition to the film former, the lipid phase contains at least one solvent that is intended to disperse and dissolve the hydrophobic film former uniformly, so that when mixed with the aqueous component, the emulsifier, and the pigment, a homogeneous mass that can be applied well is produced and a homogeneous film is formed. The solvent should be at the temperature at the application location, such as on the skin, volatile, so that a film can form quickly after application and then adhere firmly. The rapid drying of the preparation on the applied location also causes a film to form rapidly on the application location to prevent running. But the flash point must not be too low, because otherwise the solvent evaporates prematurely, creating a negative impact the shelf life, and/or evaporates too quickly, causing an unpleasant sensation on the eye. In addition, the solvent must not irritate the mucous membrane and the eye. Examples of suitable solvents are long-chain alkanes, such as isododecane, esters, volatile dimethicones, or a combination thereof. A mixture of dimethicone and trisiloxane, isononyl isononanoate, or coco-caprylate or caprinate is well suited. "Volatile" here means that the solvent evaporates at the temperature at the application location. For example, a solvent with an evaporation number (determined according to DIN 53170) of 100 or less is suitable.

The mass fraction percentage of the solvent in the total composition of the preparation according to the present invention is 10% to 40% by mass, preferably 17.5% to 35% by mass, particularly preferably 20% to 30% by mass, with the proportion of solvent introduced from the film former dispersion being included. If too small an amount of solvent is used, too little homogeneity of the hydrophobic film-forming component in the emulsion system of the present invention may result, because the hydrophobic film former cannot be sufficiently dispersed. If too much solvent is used, this can irritate the eyes. The proportion of the solvent also varies depending on the type of emulsion (water-in-oil, oil-in-water, double emulsion or microemulsion) to be formed.

Another essential component of the preparation according to the present invention is the aqueous phase, which comprises a film former based on poly(acrylate-co-styrene) and an aqueous medium. The aqueous medium is the solution/dispersant for the hydrophilic film former. It can be pure water or a mixture of water with water-soluble solvents, such as alcohol. The aqueous medium preferably consists of water.

Furthermore, the aqueous phase in the emulsion also provides for the dispersion of the other components, such as the pigments. The percentage of water depends on the type of emulsion desired, among other things. If the proportion of the aqueous medium in the overall composition is too low, the hydrophilic film former may not be distributed sufficiently homogeneously, which may lead to inhomogeneities in the resulting film. Water is also introduced into the emulsion via the film former dispersion, which usually consists of 40% to 60% by mass of water. The mass fraction of water in the overall composition of the present invention (inclusive of the water content of the film former dispersion) is suitably in a range from 20% to 65% by mass, preferably 30% to 60% by mass, particularly preferably 40% to 56% by mass.

A polymer based on poly (acrylate-co-styrene) is contained in the aqueous phase as a hydrophilic film former. It is dispersed in the aqueous phase and also contributes to the gel formation of the preparation. This polymer contributes to the advantageous properties. Its polar acrylate moiety allows it to interact with the hydrophilic ingredients and hold them in the matrix formed after application. The styrene moiety of the polymer interacts with the hydrophobic film former to aid in matrix formation. The film-forming component from the aqueous phase also contributes to increased smudge resistance as well as long-term stability at the application location. Examples of suitable hydrophilic film formers are copolymers of styrene, acrylates and ammonium methacrylates, polymers and copolymers based on polyurethane, or combinations thereof. Examples of suitable hydrophilic film formers are polyurethane 35 and styrene/acrylates/ammonium methacrylate copolymer.

Hydrophilic film-forming polymers are typically available as an aqueous dispersion, for example, with a polymer content of about 30% to 70% by mass, such as 40% to 60% by mass.

Typically, the amount of film former in the aqueous phase will depend on the type of emulsion that is required. The hydrophilic film former participates in the gel formation of the preparation and in the post-application matrix formation and contributes to the advantageous properties of the resulting film. Therefore, its share of the preparation should not be too low. If less than 8% by mass is used, a thixotropic preparation may not be possible. If the proportion of the hydrophilic film former is too high, the water resistance of the resulting film may be insufficient. Suitably, the hydrophilic film former in the preparation according to the present invention is present in a mass fraction of 3% to 30% by mass, preferably 5% to 20% by mass, particularly preferably 8% and 18% by mass.

As stated above, for the preparation according to the present invention it is essential for hydrophobic and hydrophilic film-forming polymers to interact. An emulsion preparation that is thixotropic and forms an adhesive film will be obtained only if the preparation contains all the defined components. It has been found that a preparation that contains only hydrophobic film formers or only hydrophilic film formers does not have these properties. Suitably the preparation contains hydrophobic film formers and hydrophilic film formers in a mass ratio from 3:1 to 1:3.

Depending on the proportions of film-forming polymers, the preparation is liquid or solid at room temperature. When the preparation is subjected to shearing, it becomes liquid, and the viscosity can drop to very low levels, such as 1 mPa s, for example.

A suitable dynamic viscosity for the final preparation is in a range from 100 to 900 Pa s, preferably 150 to 850 Pa s, more preferably 200 to 600 Pa s, at 25° C. in each case, and in the dormant phase, i.e. measured without shear entry. The dynamic viscosity can be determined in a conventional manner known to specialists, such as with a flat-plate or cone-plate viscometer or with another device suitable for measuring dynamic viscosity. The measurement is usually taken at room temperature, for example, 25° C. The preparation can be processed well in this viscosity range.

After the preparation according to the present invention has been applied to the eye area, it remains adhered to the applied location. To remove the preparation, it is possible to use conventional make-up removal products known to specialists, such as cotton swabs, cotton balls, make-up removal pads, or make-up removal wipes, which can be impregnated with a surfactant solution or cream, for example.

Pigments, and if necessary, additional particulates are also essential ingredients of the present invention. "Pigments" are solid colorants that do not dissolve in liquids of the preparation according to the present invention and are preferably present in micronized form. Pigments that can be used are conventional products known to specialists and used in the field of cosmetics. Examples of pigments are carbon black, activated carbon, titanium dioxide, talc, mica, feldspar, black iron oxide, red iron oxide, Berlin blue, metallic effect pigments, barium sulfate, bismuth vanadate, azo pigments, Prussian blue, sparkle gold, or polycyclic pigments, or a combination thereof. It has been found that especially carbon black and activated carbon promote the thixotropy of the preparation and pencil lead to a well covering homogeneous application. The pigments are stabilized in the preparation and remain homogeneously mixed. Stability is achieved by a combination of special film formers and an emulsifier.

The mass fraction of the pigments in the total composition of the kohl preparation can be adjusted according to the desired shade. The combination according to the present invention keeps the pigments in the dispersion and fixes them in the matrix that forms after the preparation has been applied. The preparation according to the present invention therefore makes it possible to add even greater pigment contents without the risk of separation. Depending on the opacity of the pigment(s) used in each case, the proportion can be in a range from 1% to 40% by mass, preferably from 2% to 30% by mass, particularly preferably from 3% to 20% by mass. Too small a mass fraction of the pigments can result in an insufficient color transfer or coverage of the preparation. Too high a mass fraction of pigment can result in separation and clumping of the pigment particles.

In addition to the essential components described above, the preparation according to the present invention may also contain other additives and excipients common in cosmetics, such as fillers, plasticizers, emollients, gloss-increasing agents, wetting agents, preservatives, and perfume.

Fillers serve to give the mass the desired structure. Examples are talc, kaolin, bentonite, hectorite, montmorillonite, cerium oxide, silicon oxide, boron nitride, nylon powder, polyethylene powder, polypropylene powder, silk powder and mixtures thereof, polyvalent metal soaps, non-swellable starches, natural and synthetic peeling bodies, sand, bran products, algae derivatives, thermosets, thermoplastics, elastomers, and mixtures as well as hybrids of the ingredients listed. If fillers are added to the preparation according to the present invention, they are used in the conventional amounts.

Furthermore, the preparation according to the present invention may contain at least one humectant. Suitable humectants are monohydric and polyhydric alcohols, urea derivatives, or vegetable extracts. Examples of these are butylene glycol, polyhydric alcohols and their esters, such as glycerol, diglycerol, triglycerol, diethylene glycols, amyl alcohol, hexanediol, pentaerythritol, sorbitol, xylitol, mannitol and alditol, sucrose, laureth-2 benzoate, ethylhexyl sebacate, citric acid esters such as tributyl citrate, synthetic short-chain esters, pentaerythrityl esters and oligo pentaerythrityl esters. Skin moisture can be preserved better with such moisturizers in the composition. This makes the skin look fuller and smoother.

If humectants are added to the composition of the present invention, they can be used in the conventional amount. A proportion in a range from 1% to 20% by mass, preferably 3% to 15% by mass, and particularly preferably 5% to 10% by mass, based on the total preparation, is suitable.

Furthermore, the preparation according to the present invention can contain emollients, i.e. agents that make the skin soft and supple, and/or wetting agents to wet the pigments or other particulate ingredients, for example. Examples are butylene glycol cocoate and isocetyl stearoyl stearate, which can be used in the known amounts.

Agents that increase the gloss can also be added to the preparation according to the present invention. Examples of these are esters such as C12-15 alkyl benzoate, glycol dibenzoate, propylene glycol dibenzoate, dipentaerythrityl pentaisononanoate, which can each be used in the known amounts.

The preparation according to the present invention can contain preservatives in the conventional amounts. All preservatives known to specialists in the cosmetic field are suitable here. One example of this is phenoxyethanol, which is used in a known amount.

The invention also provides a process for the production of the emulsion preparation according to the present invention in which a lipid phase comprising at least one film former based on poly(acrylate-co-siloxane) and at least one solvent, an aqueous phase comprising at least one water-soluble or water-dispersible film former based on acrylate or polyurethane and an aqueous medium, and at least one emulsifier are mixed at a temperature of 50° C. to 90° C., pigment is added, and the mass is allowed to cool.

Good results will be obtained if the mixture is stirred while it is being mixed and if a disperser is used to distribute the pigment after it is added.

This method produces a stable emulsion in which hydrophobic and hydrophilic film formers are dissolved or dispersed in a carrier liquid in each case, wherein the phases use a specific emulsifier during mixing to form an emulsion in which either droplets of the lipid phase are distributed in the aqueous phase, or droplets of the aqueous phase are distributed in the lipid phase as a continuous phase, and then the pigments are homogeneously distributed in the emulsion.

The mixing of the phases and the addition of the pigment can be done in a customary manner, using a disperser, such as a rotor/stator disperser commercially available under the name of Turrax or Ultra-Turrax. It has been found that mixing at a somewhat higher temperature, from about 50° C. to 90° C., produces a homogeneous composition. Preferably, the mixing temperature is 60° C. to 80° C., more preferably 70° C. to 80° C. Furthermore, the optimal time for the dispersing procedure is 1 to 20 minutes, preferably 2 to 15 minutes, and particularly preferably 5 to 10 minutes. Other additives can also be included. Temperature-sensitive ingredients such as fragrances or perfume are added at the end of dispersing.

After the pigments are added, the composition is allowed to cool and rest to allow a gel to form. The mass can be poured into a mold, for example. The mold can be the container in which the mass is sold or a pencil lead mold for casting pencil leads, which may then be inserted into a suitable applicator in a conventional manner. Usually for the production of pencil leads, the mass is either poured into molds and removed from the mold after cooling, or inserted into the holding parts of a rotary mechanism, or poured by a holding part directly into a corresponding mold and turned back into the rotary mechanism after cooling, or poured into a corresponding part of a rotary mechanism and allowed to solidify there.

In addition, the preparation according to the present invention can also be poured, inserted, or used in a sleeve blank to produce a pencil, such as a kohl or eyeliner pencil.

The finished preparation is easy to process, i.e. it can easily be poured into containers because it is fluid due to the thixotropy when shear is applied. It can then be stored in a tightly closed storage vessel.

The preparation according to the present invention is suitable by virtue of its properties for use in decorative cosmetics, especially for use in the eye area, as kohl or eyeliner, for example. Because of its special resistance, it is particularly suitable as kohl to be applied to the waterline, as well as for application to eyelids, lips, or other skin regions.

The invention further relates to a pencil lead for a kohl or eyeliner pencil, comprising the preparation according to the present invention in solid form. The preparation according to the present invention is in the form of a gel and can be poured to form a pencil lead. The pencil lead can be used either in a pencil or freestanding in an applicator. A pencil has an outer part and a core, wherein the outer part forms a shell, which encompasses the core. Based on current technology, the shell can be made of wood, plastic, or metal. In order to avoid premature evaporation of the solvent, the pencil should preferably have a sealed cap to prevent the solvent from escaping.

The preparation according to the present invention can also be in liquid form and in this case preferably poured into a container or casing, from which it can be removed with an applicator and applied to the desired location. One example would be dipliner. The casing can be made of metal, plastic, or glass and is preferably airtight and waterproof, and keeps the volatile components (water, solvent) from escaping.

Another object of the invention is thus the use of the emulsion preparation according to the present invention to produce a kohl or eyeliner applicator or pencil.

The preparation according to the present invention is very well suited for use on the eye in the form of a pencil or as a liquid preparation. It is easy to apply and dries quickly. It does not irritate and does not run. The resulting homogeneous film adheres very well, does not migrate away, does not smear, and is resistant to friction. Due to the fast drying, touch-up is not necessary.

The preparation according to the present invention is described based on the following examples, which, however, are not intended to be exhaustive. Where applicable, the raw materials are indicated with their INCI. Unless otherwise indicated, the information on their mass (in % by mass) is based on the total mass of the preparation.

EXAMPLES

Example 1: Kohl

The ingredients indicated in the following table were used to produce a kohl preparation according to the present invention in the form of a pigmented oil-in-water emulsion in gel form for use on the waterline. Preparations were obtained which were characterized in particular by an intense color transfer and durability, as well as a pleasant application.

This kohl preparation was made by stirring the oil phase into the aqueous phase at 75° C. Then, the pigments were added and a Turrax instrument was used for 5 to 10 minutes to disperse the mass.

| Phase | Raw material description (INCI) | Function | Mass fraction/ mass % |
|---|---|---|---|
| Interface | Polyglyceryl-6 distearate and jojoba esters and polyglyceryl-3 beeswax and cetyl alcohol | Emulsifier | 3.26 |
| Oil | Isododecane | | 22.84 |
| | Acrylates/polytrimethylsiloxymethacrylate copolymer | Film former hydrophobic | 9.79 |
| Aqueous | Water | | 39.15 |
| | Butylene glycol | | 8.16 |
| | Phenoxyethanol | Preservative | 0.48 |
| | Styrene/acrylates/ammonium methacrylate copolymer and sodium lauryl sulfate and sodium laureth-12 sulfate | Film former hydrophilic | 9.79 |
| Disperse | Carbon black | Pigment | 6.53 |
| | | Total | 100.00 |
| | Of which | Pigment | 6.53 |
| | | Oil phase | 35.89 |
| | | Aqueous phase | 57.58 |

Example 2: Viscosity Measurements

The dynamic viscosity of the preparation according to the present invention was determined using a rheometer (RheolabQC by Anton Paar) according to DIN 54453.

Some examples of the shear and the viscosity profile of the kohl compositions according to the present invention with different ratios of the film former in the aqueous phase (B) to the film former of the oil phase (A) are shown in FIG. 2.

The curve shows the viscosity based on the time, wherein a shear rate of 0.1 s$^{-1}$ was used for 120 s, then increased to 100 s$^{-1}$ for 30 s and then reduced again to 0.1 s$^{-1}$.

The rapid drop in viscosity to almost 0 at a shear rate of only 100 s$^{-1}$, as well as the rapid increase in viscosity upon completion of the shearing, demonstrate the highly pronounced thixotropy of the system. Also, the influence of the viscosity can be detected very well by selecting the ratios of the components to one another.

I claim:

1. An emulsion-based cosmetic preparation, comprising:
a lipid phase comprising a film former, wherein the film former is acrylates/polytrimethylsiloxymethacrylate copolymer, and at least one solvent, wherein the film former is present in an amount of 8% to 18% by mass of the emulsion-based cosmetic preparation;
an aqueous phase comprising a film former, wherein the film former is styrene/acrylates/ammonium methacrylate copolymer or polyurethane-35, and the aqueous phase including an aqueous medium, wherein the film former is present in an amount of 8% to 18% by mass of the preparation;
polyglyceryl-6 distearate; and
at least one pigment,
wherein the emulsion-based cosmetic preparation is in gel form having a dynamic viscosity of between 100 and 900 Pa s at 25° C.

2. The emulsion-based cosmetic preparation of claim 1, wherein the at least one solvent of the lipid phase is a volatile hydrocarbon, a volatile dimethicone, a mixture of dimethicone and trisiloxane, or a combination thereof.

3. The emulsion-based cosmetic preparation of claim 1, wherein the film former in the lipid phase and the film former in the aqueous phase are present in a ratio of from 3:1 to 1:3.

4. The emulsion-based cosmetic preparation of claim 1, wherein the at least one pigment is carbon black, activated carbon, black iron oxide, or a combination thereof.

5. The emulsion-based cosmetic preparation of claim 1, further comprising one or more of: at least one humectant, at least one preservative, and at least one scent.

6. A process for producing the emulsion-based cosmetic preparation of claim 1, comprising:
mixing into a mass, at a temperature of 50° C. to 90° C., the lipid phase comprising the film former and the at least one solvent, the aqueous phase comprising the film former and the aqueous medium, and the polyglyceryl-6 distearate;
adding the at least one pigment to the mass; and
cooling the mass to form the emulsion-based cosmetic preparation, wherein the emulsion-based cosmetic preparation has a dynamic viscosity of between 100 and 900 Pa s.

7. A pencil lead for an eyeliner pencil, comprising:
a lipid phase comprising a film former, wherein the film former is acrylates/polytrimethylsiloxymethacrylate copolymer, and at least one solvent, wherein the film former is present in an amount of 8% to 18% by mass of the pencil lead;
an aqueous phase comprising a film former, wherein the film former is styrene/acrylates/ammonium methacrylate copolymer or polyurethane-35, and the aqueous phase including an aqueous medium, wherein the film former based on acrylate or polyurethane is present in an amount of 8% to 18% by mass of the pencil lead;
polyglyceryl-6 distearate; and
at least one pigment,
wherein the pencil lead is in solid form having a dynamic viscosity of between 100 and 900 Pa s at 25° C.

8. The process of claim 6, wherein the at least one solvent of the lipid phase is a volatile hydrocarbon, a volatile dimethicone, a mixture of dimethicone and trisiloxane, or a combination thereof.

9. The pencil lead of claim 7, wherein the at least one solvent of the lipid phase is a volatile hydrocarbon, a volatile dimethicone, a mixture of dimethicone and trisiloxane, or a combination thereof.

10. The emulsion-based cosmetic preparation of claim 1, wherein the emulsion-based cosmetic preparation is at least partially thixotropic.

* * * * *